United States Patent
Jekkel et al.

(10) Patent No.: US 6,750,366 B2
(45) Date of Patent: Jun. 15, 2004

(54) MICROBIAL PROCESS FOR PREPARING PRAVASTATIN

(75) Inventors: Antonia Jekkel, Budapest (HU); Attila Konya, Szolnok (HU); Istvan Barta, Budapest (HU); Eva Ilkoy, Budapest (HU); Gyorgy Somogyi, Budapest (HU); Gabor Ambrus, Budapest (HU); Gyula Horvath, Budapest (HU); Karoly Albrecht, Budapest (HU); Istvan Szabo, Budapest (HU); Julianna Mozes Nee Suto, Budapest (HU); Janso Salat, Budapest (HU); Attila Andor, Budapest (HU); Laszlo Birinesik, Miskole (HU); Sandor Boros, Szod (HU); Ildiko Lang, Budapest (HU); Margit Bidlo Nee Igloy, Budapest (HU)

(73) Assignee: Institute for Drug Research Ltd., Budapest (HU)

(*) Notice: Subject to any disclaimer, the term of this patent is extended or adjusted under 35 U.S.C. 154(b) by 0 days.

(21) Appl. No.: 10/011,176

(22) Filed: Dec. 5, 2001

(65) Prior Publication Data

US 2002/0081675 A1 Jun. 27, 2002

Related U.S. Application Data

(62) Division of application No. 09/497,805, filed on Feb. 3, 2000.
(60) Provisional application No. 60/134,759, filed on May 18, 1999, and provisional application No. 60/118,458, filed on Feb. 3, 1999.

(51) Int. Cl.[7] ............................................. C07C 69/02

(52) U.S. Cl. ...................................................... 560/231

(58) Field of Search ........................................ 560/231

(56) References Cited

U.S. PATENT DOCUMENTS

| 4,346,227 A | 8/1982 | Terahara et al. |
| 4,537,859 A | 8/1985 | Terahara et al. |
| 5,064,817 A | 11/1991 | Yedgar et al. |
| 5,130,130 A | 7/1992 | Menez et al. |

FOREIGN PATENT DOCUMENTS

| BE | 850 090 | 3/1983 |
| EP | 0 605 230 | 7/1994 |
| JP | 58-10572 | 1/1983 |
| WO | WO 97/36996 | 10/1997 |
| WO | 98/45410 | * 10/1998 |

OTHER PUBLICATIONS

"The Therapeutic Potential of Cell–Impermeable Inhibitors of Phospholipase $A_2$" by Saul Yedgar, *J. Cellular Biochemistry*, S17D:178 (1993).

Derwent Abs. Of WO 8806445 (88–271023) Fariss et al, 1987.
Chem. Abs. 82:41565 Woelk et al., J. Neurol (1974) 207(4) 319–26.
Chem. Abs. 11:740 Regelson et al. (WO 8806445) 1987.
Chem. Abs. 118:52434 Valle et al, Abs. EP 505817 (Sep. 1992).
Chem Abs. 112:179707 Abs. JP 01180828 Miyazawa et al. (Jul. 1989).

(List continued on next page.)

Primary Examiner—Paul J. Killos
(74) Attorney, Agent, or Firm—Kenyon & Kenyon

(57) ABSTRACT

The present invention relates to a new microbial process for the preparation of the compound formula (I):

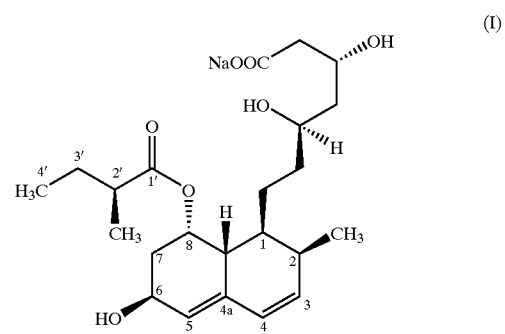

from a compound of general formula (II):

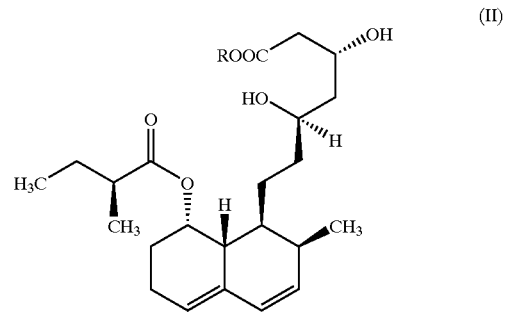

wherein R stands for an alkali metal or ammonium ion, by the submerged cultivation of a mold strain able to 6β-hydroxylate a compound of the Formula (II) in aerobic fermentation and by the separation and purification of the product of Formula (I) formed in the course of the bioconversion. The process comprises cultivating a strain of *Mortierella maculata* filamentous mold species that is able to 6β-hydroxylate a compound of the general Formula (II), on a nutrient medium containing assimilable carbon and nitrogen sources and mineral salts and separating the product formed from the fermentation broth, then isolating the compound of formula (I) and purifying the same. Novel strains of *Mortierella maculata* are also disclosed.

2 Claims, 1 Drawing Sheet

OTHER PUBLICATIONS

Chem. Abs. 103:20744 Khan et al., Acta Neurol. Scand. (1985)71(3)212–20.

Endo, A. et al., "ML–236A, ML–236B, and ML–236C, New Inhibitors of Cholesterogenesis Produced by Penicillium Citrinum," J. Antibiot 29, 1346–1348 (1976).

Endo, A. et al., "Competitive Inhibition of 3–Hydroxy–3–Methylglutaryl Coenzyme A Reductase by ML–236A and ML–236B Fungal Metabolites, Having Hypocholesterolemic Activity," FEBS Lett. 72, 323–326 (1976).

Kuo, C.H. et al., Aromatic Hydroxylation. Hydroxybenzaldehydes rom Bromobenzaldehydes via Reaction of in Situ Generated, Lithiated α–Morpholinobenzyl Alkoxides with Nitrobenzene, J. Org. Chem. 48, 1991 (1983).

Arai, M. et al., "Pravastatin Sodium (CS–514), A Novel Cholesterol–Lowering Agent Which Inhibits HMG–CoA Reductase," Sankyo Kenkyusyo Nenpo, 40, 1–38, 1988.

Koga, T. et al., "Tissue–selective Inhibition of Cholesterol Synthesis in Vivo by Pravastatin Sodium, a 3–Hydroxy–3–methylglutaryl coenzyme A Reductase Inhibitor," Biochim. Biophys. Acta, 1045, 115–1120, 1990.

A.T.M., Serajuddin et al., "Relative Lipophilicites, Solubilities, and Structure–Pharmacological Considerations of 3–Hydroxy–3–Methylglutaryl–Coenzyme A (HMG–CoA), Reductase Inhibitors Pravastatin, Lovastatin, Mevastatin, and Simvastatin," J. Pharm. Sci. 80, 830–834, 1991.

Serizawa et al., "Microbial Hydroxylation of ML–236B (Compactin) Studies on Microorganisms Capable of 3β–Hydroxylation of ML–236B," J. Antibiotics, 36, 887–891, 1983.

Hosobuchi, M. et al., "Application of Computer to Monitoring and Control of Fermentation Process: Microbial Conversion of ML–236B Na to Pravastatin," Biotechnology and Bioengineering, 42, 815–820, 1993.

Matsuoka et al., "Purification and Characterization of Cytochrome P–450sca from Streptomyces Carbophilus," Eur. J. Biochem. 184, 707–713, 1989.

Zycha, H. und Siepmann, R, Mucorales, "Eine Beschreibung aller Gattungen und Arten dieser Pilzgruppe", D–3301 Lehre, Verl. Von J. Cramer. 1969. Copy of book not enclosed.

* cited by examiner

MICROBIAL PROCESS FOR PREPARING PRAVASTATIN

This application is a division of U.S. patent application Ser. No. 09/497,805, filed Feb. 3, 2000, which claims the benefit, under 35 U.S.C. §119(e) of U.S. Provisional applications No. 60/118,458, filed on Feb. 3, 1999, and No. 60/134,759, filed May 18, 1999.

FIELD OF THE INVENTION

The present invention relates to a process for the preparation of pravastatin, and particularly to a microbial process for the manufacture of pravastatin on an industrial scale.

BACKGROUND OF THE INVENTION

The highest risk factor of atherosclerosis and especially coronary occlusion is the high cholesterol level of the plasma. In the last two decades 3-hydroxy-3-methylglutaryl coenzyme A reductase (EC.1.1.1.34) as the rate limiting key enzyme of the cholesterol biosynthesis was extensively examined. Pravastatin, a compound of Formula I,

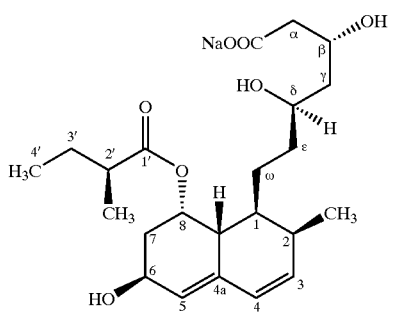

and other related compounds (compactin, mevinolin, simvastatin) are the competitive inhibitors of the HMG-CoA reductase enzyme [A. Endo et al., J. Antibiot. 29, 1346–1348 (1976); A. Endo et al., FEBS Lett. 72, 323–326 (1976); C. H. Kuo et al., J. Org. Chem. 48, 1991 (1983)].

Pravastatin was first isolated by M. Tanaka et al. (unpublished results) from the urine of a dog during the examination of the compactin metabolism (Arai, M. et al., Sankyo Kenkyusyo Nenpo, 40, 1–38, 1988). Currently pravastatin is a cholesterol lowering agent with the most advantageous action mechanism in the therapy. Its most important character is tissue selectivity, i.e., it inhibits the cholesterol synthesis at the two main sites of the cholesterogenesis, such as in the liver and in the small intestine, while in other organs the intracellular enzyme limiting effect is hardly detectable, At the same time the cholesterol biosynthesis limiting effect of mevinolin and simvastatin is significant in most of the organs (T. Koga et al., Biochim. Biophys. Acta, 1045, 115–120, 1990).

Pravastatin essentially differs in chemical structure from mevinolin and simvastatin which have more lipophilic character. In the case of the latter compounds the substituent connected to the C-1 carbon atom of the hexahydronaphthalene skeleton is ended in a 6-membered lactone ring, while in the case of pravastatin, instead of the lactone ring, the biologically active, opened dihydroxy acid sodium salt form is present. Another important structural difference is that instead of the methyl group of mevinolin and simvastatin at the C-6-position of the hexahydronaphthalene ring, a hydroxyl group can be found in pravastatin, which results in a further increase in its hydrophilic character.

As a result of the above structural differences pravastatin is able to penetrate through the lipophilic membrane of the peripheral cells only to a minimal extent (A. T. M., Serajuddin et al., J. Pharm. Sci. 80, 830–834, 1991).

Industrial production of pravastatin can be achieved by two fermentation processes. In the first, microbiological stage compactin is prepared, then in the course of a second fermentation the sodium salt of compactin acid as a substrate is converted to pravastatin by microbial hydroxylation at the 6β-position.

According to published patents, the microbial hydroxylation of compactin can be accomplished to various extents with mold species belonging to different genera, and with filamentous bacteria belonging to the Nocardia genus, with Actinomadura and Streptomyces genera (Belgian patent specification No. 895090, Japanese patent specification No. 5,810,572, U.S. Pat. Nos. 4,537,859 and 4,346,227 and published European patent application No. 0605230). The bioconversion of compactin substrate was published in a 500 μg/ml concentration using filamentous molds such as *Mucor hiemalis*, *Syncephalastrum nigricans*, *Cunninghamella echinulata* and in 2000–4000 μg/ml with Nocardia, Actinomodura and Streptomyces strains belonging to the prokaryotes.

A general problem experienced in the cases of manufacturing the pravastatin with filamentous molds is that due to the antifingal effect of compactin, the microorganisms are not able to tolerate the compactin substrate fed to the culture even at low concentrations (Serizawa et al., J. Antibiotics, 36, 887–891, 1983). The cell toxicity of this substrate was also observed in the hydroxylation with *Streptomyces carbophilus* extensively studied by Japanese researchers (M. Hosobuchi et al., Biotechnology and Bioengineering, 42, 815–820, 1993).

Japanese authors tried to improve the hydroxylating ability of the *Streptomyces carbophilus* strain with recombinant DNA techniques. A cytochrome P-450 monooxygenase system is needed for the hydroxylation of compactin (Matsuoka et al., Eur. J. Biochem. 184, 707–713, 1989). However, according to the authors, in the bacterial cytochrome P-450 monooxygenase system not one but several proteins act in the electron transport, which aggravate the application of the DNA techniques. Development of a cost-effective microbiological hydroxylation method for the manufacture of pravastatin is an extremely difficult, complex task.

The aim of the present invention is to elaborate a new microbial process for the preparation of pravastatin from compactin in industrial scale, which would produce pravastatin at more advantageous conditions than those previously known. During our research work, above all we tried to find a microorganism strain with a hydroxylase enzyme that can be adapted for the microbial transformation of compactin to pravastatin in a high concentration.

SUMMARY OF THE INVENTION

The present invention relates to a microbial process for the preparation of the compound of formula (I)

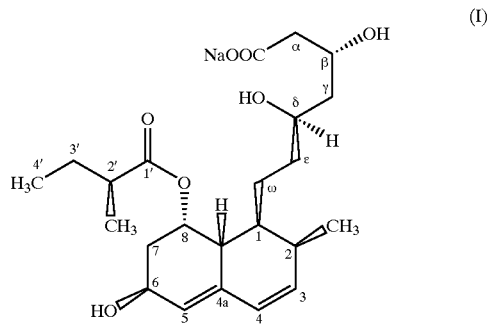

from a substrate compound of formula (II),

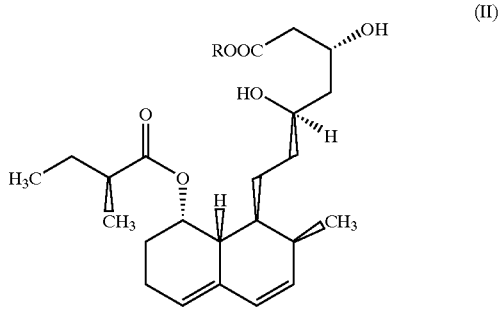

(II)

wherein R stands for an alkali metal or ammonium ion, comprising the steps of (a) cultivating a strain of *Mortierella maculata* filamentous mold species able to 6β-hydroxylate a compound of formula (II) on a nutrient medium containing assimilable carbon- and nitrogen sources and mineral salts, (b) feeding the substrate to be transformed into the developed culture of *Mortierella maculata*, (c) fermenting the substrate until the end of bioconversion, (d) separating the compound of formula (I) from the culture broth, and (e) isolating the compound of formula (I).

The present invention also relates to a biologically pure culture of the *Mortierella maculata* n. sp. E-97 strain deposited at the National Collection of Agricultural and Industrial Microorganisms, Budapest, Hungary under accession number NCAIM(P)F 001266 and a biologically pure culture of its mutant, the *Mortierella maculata* n. sp. E-97/15/13 strain deposited at the National Collection of Agricultural and Industrial Microorganisms, Budapest, Hungary under accession number NCAIM(P)F 001267.

DETAILED DESCRIPTION OF THE INVENTION

Figure 1:
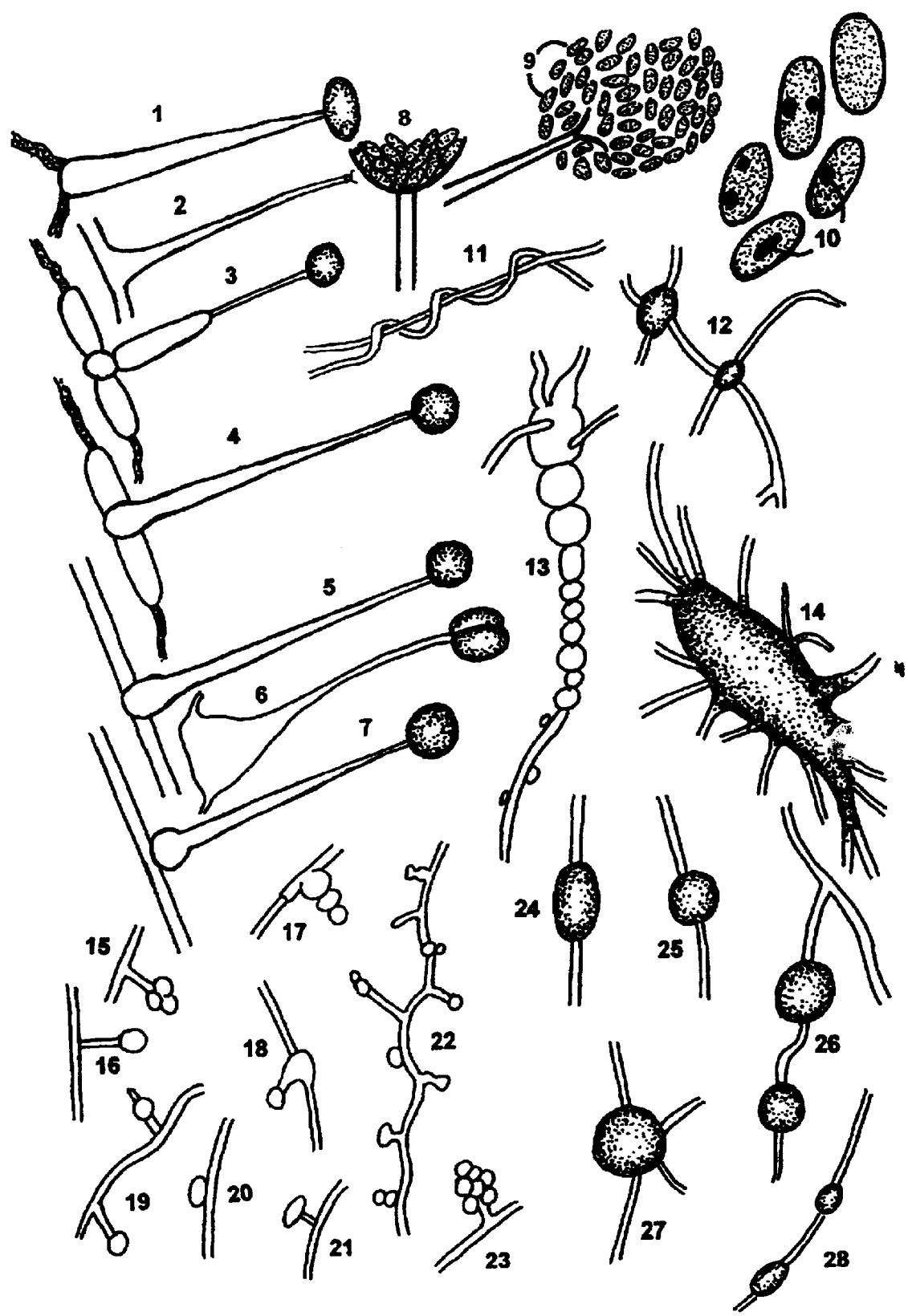
FIG. 1 is an illustration of the physical characteristics of *Mortierella maculata* n. sp. E-97.

In the course of our screening program, which covered about 5500 prokaryotic and eukaryotic strains, 23 microorganisms were selected, which were able to hydroxylate compactin in opposition. Among these strains a filamentous mold proved to be more appropriate for the production of pravastatin due to its higher resistance against compactin as compared to the strains known from published patents. According to the taxonomic investigation, this strain proved to be a new representative of the species belonging to the Mortierella genus (*Mortierella maculata* n. sp.). From the selected molds a new strain was isolated on the one hand by the application of the mutation-selection methods, and on the other hand by the induction of the hydroxylase enzyme of the strain, which one was able to hydroxylate the compactin substrate to pravastatin in a higher concentration than published so far. As mutagenic agents, physical and chemical mutagens were applied (UV irradiation, methyl methane sulfonate, N-methyl-N'-nitro-N-nitrosoguanidine). After the mutagenic treatments, in order to prepare haploid cells, the spore suspension was spread on benomyl-containing agar plates, then in order to induce the hydroxylase enzyme the developed colonies were inoculated onto 100 μg/ml 8-de-(2-methyl-butyryl)-compactin-containing or compactin-containing agar plates. By the application of these methods a mutant strain was prepared from the new strain that is able to convert compactin to pravastatin to a significantly higher extent than the parent strain.

In the course of the optimizing experiments we determined the composition of the most beneficial inoculum, and the most advantageous bioconversion media for the compactin hydroxylation, as well as the optimal method for the repeated feeding of compactin in a high concentration.

Consequently, this invention is based on the recognition that the E-97 and E-97/15/13 designated strains of the isolated mold named *Mortierella maculata*, which were deposited under accession numbers of NCAIM(P)F 001266 and NCAIM(P)F 001267 respectively, at the National Collection of Agricultural and Industrial Microorganisms (Department of Microbiology and Biotechnology, University of Horticulture and the Food Industry Budapest), under appropriate fermentation conditions are able to manufacture pravastatin to a high extent, while the undesired related compounds such as the acid forms of 6α-hydroxy-compactin, 2α-hydroxy-compactin, 8-de-(2-methyl-butyryl)-compactin, 3α,5β-dihydroxy-5,6-dihydro-isocompactin, 8a,β-hydroxy-compactin and the hydroxylated derivatives at positions 2 and 3 of the 2-methyl-butyryl side chain of compactin are obtained only in small or trace amounts during the bioconversion. Thus, these strains are especially appropriate for manufacturing pravastatin in an industrial scale.

Taking into account that the economical manufacture of the active ingredient on an industrial scale is a function of the compactin substrate concentration, it is important to have a strain that is able to tolerate high compactin and pravastatin concentrations. Consequently, a further important part of the invention is the recognition that the hydroxylating ability of the original mold isolate can be improved by the application of mutation-selection and enzyme induction methods and, furthermore, that by the development of an appropriate method for substrate feeding the hydroxylation of large quantities of compactin to pravastatin can be executed in a single procedure. In conclusion, the new mutant strain designated as *Mortierella maculata* n. sp. E-97/15/13 is especially appropriate for the manufacture of pravastatin.

Taxonomic features of the isolated new mold species comparing it to the most important diagnostic attributes of the known *Mortierella species* are summarized below.
Taxonomic description of the holotype strain *Mortierella maculata* nov. spec. E-97

On starch-casein-malt extract-agar media the aerial mycelium is well developed (more than 10 μm thick covering layer over the substrate mycelium). At the beginning it appears as a tightly woven white web of hyphae, in which later yellowish sporulating spots with a few mm diameter sparsely appear (new name "maculatus" refers to the above: spotted). This yellowish coloration can sometimes occupy the larger continuous surfaces of the aerial web. The color of the substrate mycelium is on Czapek-, bloody-Czapek-, tyrosine-, starch-casein-, malt extract-, etc. agar media mostly colorless or light yellowish. The color of the substrate mycelial web is light reddish on yeast extract-glucose-peptone medium. Production of diffusible and soluble pigments on the above listed media is not experienced, or only rarely an insignificant yellowish coloration occurs on these media. Colonies of strain E-97, due to their volatile oil production and similarly to many other species of Mortierella, (except to species of section Isabellina), can exude a very characteristic strong scent.

Sporangiophores, designated by reference numerals 1–7 in FIG. 1, frequently develop locally on the aerial hyphae (but less on the substrate ones) in great numbers at very different distances from each other. They are not branching, but are mostly straight or curved. Their length is generally between 60–80 µm. The starting point in the overwhelming majority of cases is a more or less short but strongly swollen hyphal section of the aerial web, from which they are separated by walls. Sporangiophores themselves can be also swollen (sometimes strongly), as shown by reference numeral 6, but in the direction of the sporangium they gradually narrow, from 5.0–9.0 µm to 1.0–2.0 µm. It is an important taxonomic character that below the sporangiophores they never broaden out (see reference numeral 8).

Sporangia are spherical; in some cases slightly flattened spheres. Their diameter is about 6.0–17.0 µm, relatively small compared to the measures of sporangia of other Mortierella species. Sporangia may contain many spores, but sporangia bearing only one spore also exist. The spores 9 are cylindrical or less oval. Their size is 3.0–5.0×1.5–2.0 µm. Within the individual spores one or two small dark spherical oil-drops 10 may be present. Due to the very easy disintegration of the wall of sporangia, in wet surroundings the spores will quickly be scattered. After the disintegration of the sporangium, sometimes at the end of the sporangiospores, a fine pitchfork-like "collar" and a very short rudimental (and not typical) columella can be observed. Gemmae 15–28 that are spherical or cylindrical may occur on most different diagnostic media. Usually the size is 10–25 µm. In the cultures chains of spherical gemmae 13, budding cells, intercalated gemmae 15–23, hyphal associations of particular spiral-growth of one hypha around the other 11, anastomotic-like structures and giant cells, etc. can also be found. In the aerial mycelium also large (50–250 pm diameter) very dense hyphal webs 14 can be seen but without the presence of detectable zygotes.

Cultures of strain E-97 are able to reduce nitrates to nitrites, do not hydrolyze starch, esculin, arginine or gelatine but hydrolyze Tween polysorbates and do not decompose paraffin hydrocarbons. The cultures of strain E-97 have urease activity show a good growth between pH 7.0 and 9.0 tolerate a maximum 2% NaCl. The effect of xanthine, hypoxanthine, lecithin, tyrosine and adenine are negative. A strong acid production of the cultures has been detected from glucose, fructose, glycerine and galactose, but very weak or no production from xylose, arabinose, raffinose, sorbitol, inositol, inulin, etc. Weak growth is detected on pyruvate and acetate but no growth could be found with benzoate, salicylate, citrate, lactate, succinate, tartarate and malonate. A good growth was observed with glucose and fructose as sole carbon-sources in the medium. Utilization tests with xylose, arabinose, rhamnose, sucrose, raffinose, mannitol and inositol proved to be negative. The cultures do not decompose cellulose.

Systematic position

Strain E-97 belongs to the family Mortierellaceae and it is a typical member of the genus Mortierella: sporangia contain generally many spores, columella is extremely reduced, gemmae are frequently present, the occurrence of zygotes has not been detected and the colonies exude a very characteristic strong scent. Within the genus Mortierella, strain E-97 is a typical representative of the "Section Alpina." The latter can be characterized by very short non-branching sporangiophores (maximal length to 200 µm), and minute sporangia (Zycha, H. und Siepmann, R, Mucorales. Eine Beschreibung aller Gattungen und Arten dieser Pilzgruppe. D-3301 Lehre, Verl. von J. Cramer. 1969). Among the members of the section Alpina, strain E-97 shows the greatest similarity to the species *M. thaxteri* Bjorling 1936 and *M. renispora* Dixon-Stewart 1932. However, the data in the Table I clearly show the differences in diagnostic properties of strain E-97 and of these two species. Accordingly, as a new species herewith we introduce the strain under the name *Mortierella maculata* nov. spec. E-97.

TABLE 1

A comparison of the holotype strain E-97 of *Mortierella maculata* n.sp. with the species *M. renispora* and *M. thaxteri* on the basis of key diagnostic properties

|  | *Mortierella renispora* | Mortierella strain E-97 | *Mortierella thaxteri* |
|---|---|---|---|
| Origin of sporangiophores | Ordinary, however the hyphae are wider than the regular ones, laterally from broadened swollen hyphae. | Laterally from (swollen or normal) aerial hyphae or not separated sections of substrate hyphae. | Laterally from swollen separated segments of aerial hyphae or not separated segments of substrate hyphae |
| Shape and size of sporangiophores | Gradually decreasing towards the top from 10 µm to 3 µm. Length is about 200 µm. | Mostly straight or curved, not branching. Width gradually decreasing towards the tip: from 5–9 µm to 1.5–2.5 µm. Length is about 60–80 µm. At the tip never broadened. | Length about 60–90 µm. Width at the starting point is about 5–7 µm, at the tip it is reduced to 1.5–2 µm. Immediately under the sporangium broadened out |
| Shape and size of sporangia | Colorless, diameter is 25 µm. | Mostly spherical (6–17 µm diam.) but rarely less flattened. Generally contain many spores, rarely one spore. | Spherical (12–20 µm diam.). They contain many spores but on certain media there is also only one spore-bearing sporangra. |
| Wall (membrane) of the sporangia | Spreading membrane. After disintegration remains a collar-like structure. | Disintegrating. A pitchfork-like collar remains, | Disintegrating, a minute backward-bending collar remains. |
| Shape and size of the spores | Roughly kidney-shaped. hyaline structures, sizes are 2 × 4 µm. | Cylindrical. Length (3–5 µm) can doubly exceed the width (1.5–2 µm). | Ellipsoidal hyaline spores of 3.5–4 × 1.5–2 µm) dimension. |
| Gemmae | Occur on the most different media | Frequent on very different media, mostly in the aerial mycelium. Spherical or elongated (10–25 µm). | Intercalary, oval gemmae (10–14 µm) in the substrate mycelium. |
| Zygotes | Frequent on all diagnostic media. Diameter together with the covering hyphae is about 500 µm, without them about 30 µm. | Not detected. | Not observed. |

TABLE 1-continued

A comparison of the holotype strain E-97 of *Mortierella maculata* n.sp.
with the species *M. renispora* and *M. thaxteri* on the basis of key diagnostic properties

| | Mortierella renispora | Mortierella strain E-97 | Mortierella thaxteri |
|---|---|---|---|
| Dense foci of the hyphal web | | Large densely woven hyphal foci (50–250 μm) frequent but without zygotes. | In old cultures large (100–125 μm diam) yellowish-grey dense hyphal webs, without zygote. |
| Color and habit of the aerial mycelium | Loose, always white hyphal web | White with yellowish spots. | At first spider's web-like, later more dense. |

In the process for the preparation of pravastatin according to the present invention, preferably the culture of the mold strain designated as *Mortierella maculata* n. sp. E-97 or its mutant designated as E-97/15/13 is used. The selected strain is highly advantageous due to its fast growth. As a carbon source it easily utilizes glucose, glycerine, fructose, or galactose. As a nitrogen source yeast extract, peptone, casein, meat extract, soybean meal, corn steep liquor, sodium nitrate, or ammonium sulfate can be used.

In the culture media used for the production of pravastatin besides the above carbon and nitrogen sources mineral salts, e.g., potassium dihydrogen phosphate, magnesium chloride, magnesium sulfate, trace elements (ferrous, manganous salts), amino acids and antifoaming agents, can be present.

According to a preferred embodiment of the present invention, the spore suspension having been prepared from the slant agar culture of the *Mortierella maculata* n. sp. designated as E-97 strain or its mutant [NCAIM(P)F 001267] designated as E-97/15/13, is seeded into an inoculum medium; then 10% of the inoculum culture, which is cultivated for 3 days at about 25–30° C., preferably at about 24–28° C., most preferably at about 28° C., is transferred into the bioconversion medium. Then it is incubated for 4 days at about 25–28° C., preferably at about 28° C., then glucose and the sodium salt of compactin acid are fed into the culture. Depending on the concentration of the fed compactin substrate, the cultivation is continued for 2–12 days further under aerobic conditions, while the pH is maintained between 5.5 and 7.5, preferably at 7.0. The bioconversion is done under stirred and aerated conditions, when the air flow rate is 0.2 vvm, the spinning rate of the stirrer is 400/min.

In the course of the fermentation the bioconversion of compactin substrate was followed by a high pressure liquid chromatographic method (HPLC). According to this method, the sample of the broth is diluted twofold with methanol and centrifuged, and the supernatant is used for the HPLC analysis under the following parameters: Waters analytical HPLC equipment; column: Nucleosil $C_{18}$ 10 μm; detection wavelength: 238 nm; injection volume: 20 μl, flow rate: 1 ml/min; gradient elution is used, eluents: A=0.05% aqueous solution of phosphoric acid, B=acetonitrile.

Elution gradient:

| Time (min) | Eluent A (%) | Eluent B (%) |
|---|---|---|
| 0 | 70 | 30 |
| 20 | 0 | 100 |
| 25 | 0 | 100 |
| 25.1 | 70 | 30 |
| 35 | 70 | 30 |

Approximate retention times: pravastatin 8.6–9.0 min; compactin acid 11.6–12.0 min; pravastatin lactone 15.0–15.5 min, compactin 16.5–17.0 min.

For the production of pravastatin the aqueous solution of the sodium salt of compactin acid is added at the 96th hour of the cultivation. For this procedure the substrate is prepared in solid form as follows. Compactin lactone is hydrolyzed in a 0.2M sodium hydroxide solution for 2 hours at 40° C. then the pH of a reaction mixture is adjusted to 7.5 by hydrochloric acid and the neutralized solution is layered on a Diaion HP-20 adsorbent column; the sodium chloride formed during the neutralization is eliminated by aqueous washing of the column, and then the sodium salt of the compactin acid is eluted from the column by 50% aqueous acetone. Thereafter the eluate is distilled in vacuum and the aqueous residue is lyophilized. After neutralization the aqueous solution of the alkaline hydrolysate of compactin can also be directly used as substrate. In this case the compactin acid sodium salt content of the hydrolysate is measured by HPLC, and the solution is kept at −20° C. until being applied.

The higher the broth pH reached by the fourth day of the fermentation, the more advantageous for the hydroxilation of the compactin substrate. Feeding of the compactin substrate is allowed to be started when the pH of the broth exceeds 6.3. At the 4th day of the fermentation as much of the sterile filtered aqueous solution of compactin acid sodium salt is added as needed to reach the 500 μg/ml concentration. Glucose is also fed to the culture from its 50% solution sterilized at 121° C. for 25 minutes as follows: if the pH of the broth is higher than 6.7 value, 1% glucose is added related to the volume of the broth, while if the pH is within the 6.3–6.7 range the quantity of the glucose fed is 0.5% Compactin acid sodium salt is consumed from the broth after 24 hours, its transformation is analyzed by HPLC measurement. In this case, for each ml of the broth another 500 μg of compactin is added. Besides the compactin substrate, glucose is also fed as described above. Morphology of the 120 hour culture is characterized by the small pellet growth (diameter of the pellet; 0.5–3.0 mm). After 24 hours the second dose of substrate is also consumed from the broth, thus a further portion of compactin acid sodium salt producing a 500 μg/ml concentration of it in the whole broth is added parallel with the glucose feeding dependent on the pH value of the broth. From the 4th day of the fermentation the substrate and the glucose feeding is repeated in daily frequency as it is written before until the 17th–18th day of the fermentation.

For the recovery of the product from the broth, it is advantageous to take into consideration the fact that during the bioconversion pravastatin is formed in its acidic form, thus it can be isolated from the filtrate of the broth by its adsorption on an anion exchange resin column. For the isolation of the product it is advantageous to use a strongly basic anion exchange resin which is a polystyrene-divinylbenzene polymer carrying quaternary ammonium active groups. The product can be adsorbed directly from the filtrate of the broth by mixing the anion exchange resin being in hydroxyl form into it. The product being adsorbed on the ion exchange resin can be eluted from the column by acetic acid or a sodium chloride-containing acetone-water mixture, preferably 1% sodium chloride containing acetone-water (1:1) mixture. Pravastatin-containing fractions are combined and the acetone being in the eluate is distilled off in vacuum. The pH of the concentrate is adjusted with 15% sulfuric acid into the range of 3.5–4.0 and the aqueous solution is extracted by ethyl acetate. The ethyl acetate extract is washed with water and dried with anhydrous sodium sulphate. Then the lactone derivative is prepared from pravastatin. The lactone ring closure is carried out in dried ethyl acetate solution at room temperature, under continuous stirring by inducing the lactone formation with trifluoroacetic acid being present in catalytic quantity. The transformation procedure is checked by thin layer chromatographic analysis (TLC). After finishing the lactone formation the ethyl acetate solution is washed at first with 5% aqueous sodium hydrogen carbonate solution and then with water, then it is dried with anhydrous sodium sulfate and evaporated in vacuum. The evaporated residue is treated in acetone solution with charcoal, then evaporated again and recrystallized from a 1–4 carbon atom-containing aliphatic alcohol, preferably from ethanol. The evaporation residue of the recrystallization mother liquor is purified with silica gel column chromatography applying the mixture of ethyl acetate-n-hexane with gradually increasing ethyl acetate content as the eluent.

From the pravastatin lactone obtained after recrystallization and chromatographic purification pravastatin is prepared by hydrolysis at room temperature in acetone with equivalent quantity of sodium hydroxide. When the pravastatin sodium salt formation is completed, the reaction mixture is diluted with water and neutralized, and the acetone content is distilled in vacuum. Pravastatin is adsorbed from the obtained aqueous residue on a Diaion HP-20 resin-containing column, washed with deionized water and eluted from the column with an acetone-deionized water mixture. Then the pravastatin containing fractions are combined, the acetone content is distilled off and after the lyophilization of aqueous residue pravastatin can be obtained in high purity, which can be recrystallized from an ethyl acetate-ethanol mixture.

In the course of the procedure the whole quantity of pravastatin can be adsorbed. During the lactone closure of pravastatin 3α-hydroxy-iso-compactin and other by-products can also be formed. Although these latter reactions decrease the yield of the isolation but those compounds can be separated by the above-described purification method and consequently, pravastatin can be manufactured this way in a pharmaceutically acceptable quality.

After finishing the bioconversion pravastatin can be extracted either from the fermentation broth or from the filtrate obtained after the separation of the filamentous mold cells. Filamentous mold cells can be eliminated either by filtration or centrifugation; however, it is advantageous especially on an industrial scale to make a whole broth extraction. Before extraction the pH of either the fermentation broth or the filtrate of the broth is adjusted to 3.5–3.7 with a mineral acid preferably with diluted sulfuric acid. The extraction is done with an ester of acetic acid and a 24 carbon atom containing aliphatic alcohol, preferably with ethyl acetate or isobutyl acetate. Extraction steps should be done very quickly in order to avoid the formation of the lactone derivative from pravastatin at acidic pH.

From the organic solvent extract the pravastatin in acid form can be transferred as the sodium salt into the aqueous phase. For example, from an ethyl acetate extract pravastatin can be extracted by 1/10 and 1/20 volume ratio of 5% sodium hydrogen carbonate or weakly alkaline water (pH 7.5–8.0). It was found that pravastatin can be recovered in a pure form from the above-obtained alkaline aqueous extract by column chromatography with the application of a non-ionic adsorption resin. An advantageous method is to first remove the solvent dissolved in the aqueous phase by vacuum distillation from the alkaline aqueous extract, and then the aqueous extract is loaded on a Diaion HP-20 column.

Pravastatin sodium salt being adsorbed on the column is purified by elution increasing gradually the acetone content of the aqueous solutions, then the pravastatin-containing main fractions are combined and concentrated in vacuum. The aqueous concentrate is purified further by chromatography on another Diaion HP-20 column, obtaining an eluate containing pure pravastatin, from which after clarification with charcoal and lyophilization pravastatin can be obtained in a pharmaceutically acceptable quality.

This isolation procedure consists of fewer stages than the previous one, since the lactone formation of pravastatin and its hydrolysis are not involved in the procedure. During the isolation pravastatin is exposed to acidic condition for only a limited time, under which it is less stable than in neutral or alkaline solutions, consequently, during this isolation procedure artefacts are practically not formed.

Furthermore, it was found that the chromatography on Sephadex LH-20 Dextran gel (hydroxypropylated derivative) is advantageously used for purifying pravastatin. By application of this method pravastatin exceeding the purity of 99.5% (measured by HPLC) can be produced.

In the course of our experiments it has been recognized that from the organic solvent extract, preferably from the ethyl acetate or isobutyl acetate extract of the broth or the broth nitrate of the filamentous mold or the filamentous bacteria strains among them the *Mortierella maculata* n. sp. strain able to 6β-hydroxylate a compound of general formula (II), pravastatin can be precipitated as a crystalline salt with secondary amines. Further it was found that for the salt formation several secondary amines containing alkyl, cycloalkyl-, aralkyl- or aryl-substituents are appropriate. Expediently non-toxic secondary amines were selected among them, e.g., dioctylamine, dicyclohexylamine, dibenzylamine. The isolation of the organic secondary amine salt intermediates, e.g., the dibenzylamine salt was carried out by adding dibenzylamine in 1.5 equivalent quantity related to the pravastatin content of the extract, then the extract is concentrated by vacuum distillation to 5% of its original volume, then another quantity of dibenzylamine is added into the concentrate in 0.2 equivalent ratio. The crystalline dibenzylamine salt is precipitated from the concentrate. The crystalline crude product is filtered and dried in vacuum. Then it is clarified with charcoal and recrystallized in acetone.

In the procedure mentioned earlier in which the organic solvent extraction and the reextraction at alkaline pH are involved, the isolation method based on the secondary amine salt formation can be used also for the replacement of the column chromatographic purification. In this case it is advantageous to precipitate the pravastatin dibenzylamine salt from the isobutyl acetate extract obtained after the acidification of the alkaline aqueous extract.

Pravastatin organic secondary amine salts can be transformed to pravastatin by sodium hydroxide or a sodium alkoxide, preferably sodium ethoxide.

The transformation is detailed in the case of pravastatin dibenzylamine salt. The recrystallized dibenzylamine salt is suspended in an isobutyl acetate-water mixture, then equivalent quantity of sodium hydroxide is added in aqueous solution to the suspension by maintaining under stirring the pH in the range of 8.0–8.5. After disappearance of the suspension the phases are separated and the pravastatin-containing aqueous solution is washed twice with isobutyl acetate. The aqueous solution is clarified with activated carbon and lyophilized yielding pravastatin in a pharmaceutically acceptable quality.

One preferred method for the transformation of pravastatin dibenzylamine salt to pravastatin is to suspend the recrystallized dibenzylamine salt in ethanol, then equivalent quantity or small excess of sodium ethoxide is added under stirring to the suspension, then the reaction mixture is concentrated in vacuum and by adding acetone the pravastatin is precipitated in crystalline form from the concentrate.

Another preferred method for the transformation of pravastatin dibenzylamine salt to pravastatin is to dissolve the recrystallized dibenzylamine salt in ethyl acetate-ethanol mixture and by adding equivalent quantity or small excess of sodium hydroxide in ethanol to the solution pravastatin is precipitated.

The isolation of pravastatin via a secondary amine salt intermediate is a simpler procedure than any previously known isolation procedures. During the procedure artifacts are not formed, and the separation of pravastatin from the by-products of the bioconversion and from the various metabolic products biosynthesized by the hydroxylating microorganism can be solved without the application of any chromatographic methods.

The structures of pravastatin, pravastatin lactone and the isolated secondary amine salts of pravastatin have been proven by UV, IR, $^1$H-NMR, $^{13}$C-NMR and mass spectroscopic methods.

EXAMPLES

The invention will be more fully described and understood with reference to the following examples, which are given by way of illustration and are not intended to limit the scope of the invention in any way.

Example 1

A spore suspension was prepared with 5 ml of a 0.9% sodium chloride solution obtained from a 7–10 day old, malt extract-yeast extract agar slant culture of *Mortierella maculata* nov. spec. E-97 [NCAIM(P)F 001266] strain able to 6β-hydroxylate compactin and the suspension was used to inoculate 100 ml inoculum medium PI sterilized in a 500 ml Erlenmeyer flask.

Composition of the medium PI:

| | |
|---|---|
| glucose | 50 g |
| soybean meal | 20 g |
| in 1000 ml tap-water. | |

Before the sterilization the pH of the medium was adjusted to 7.0, then it was sterilized at 121° C. for 25 min. The culture was shaken on a rotary shaker (250 rpm, 2.5 cm amplitude) for 3 days at 28° C., then 10 ml of the obtained culture was transferred into 100–100 ml bioconversion media MU/4 sterilized in 500 ml Erlenmeyer flask for 25 min at 121° C.

Composition of the medium MU/4:

| | |
|---|---|
| glucose | 40 g |
| soybean meal | 20 g |
| casein-peptone | 1 g |
| asparagine | 2 g |
| potassium dihydrogen phosphate | 0.5 g |
| in 1000 ml tap-water. | |

Before the sterilization the pH of the medium was adjusted to 7.0, then it was sterilized at 121° C. for 25 min.

Flasks were shaken on a rotary shaker (250 rpm, 2.5 cm amplitude) for 4 days at 25° C., then 50–50 mg compactin substrate (compactin acid sodium salt) was added in sterile-filtered aqueous form into the cultures, then the cultivation was continued. Similarly, at the 5th day another 50–50 mg compactin acid sodium salt was added into the mold cultures, and the fermentation was continued for a further 24 hours. The pravastatin content of the broth was determined by HPLC. The fermentation was continued for 168 hours. At the end of the bioconversion the average pravastatin concentration of the fermentation broth was 620 μg/ml.

Example 2

In a laboratory scale fermenter with 5 liters working volume a MU/S bioconversion culture medium is prepared, the components of the culture medium are added corresponding to 5 liters, volume but it was loaded up only to 4.5 liters, then it was sterilized for 45 min at 121° C. and seeded with 500 ml of the inoculum culture made according to the Example 1.

Composition of medium MU/8:

| | |
|---|---|
| glucose | 20 g |
| glycerine | 20 g |
| soybean meal | 20 g |
| peptone | 5 g |
| potassium dihydrogen phosphate | 0.5 g |
| polypropyleneglycol 2000 | 1 g |
| in 1000 ml tap water. | |

Before sterilization the pH of the medium was adjusted to 7.0 value.

The fermentation was carried out at 28° C., with a stirring rate of 400 rpm and with an aeration rate from bottom direction 60 liters/hour for 4 days. At the 2nd day after the transfer the culture started to foam heavily, which can be decreased by the addition of further polypropyleneglycol 2000. At the beginning of the fermentation (16–20 hours) the pH decreased from the initial value of 6.5 to 5.0–5.5, then from the 3rd day it started to increase and reached 6.3–7.5 by the 4th day. The feeding of the compactin substrate is allowed to be started if the pH of the broth is above 6.3. At the 4th day of the fermentation 2.5 g compactin substrate is added in sterile filtered aqueous solution. Calculated for the volume of the broth 0.5–1.0% glucose was added into the culture depending on the pH in the form of 50% solution sterilized at 121° C. for 25 minutes in parallel with the substrate feeding. After 24 hours the compactin substrate is consumed from the culture, which is detected by HPLC from the samples taken from the fermenter. In this case another 2.5 g compactin substrate and glucose were added as described above, and the bioconversion was continued for 24 hours further when the substrate was converted to pravastatin.

After finishing the fermentation, 5.1 liters broth containing 630 µg/ml pravastatin were filtered on a filter cloth. Two liters water were added to the separated mycelium, then the mycelium suspension was stirred for one hour and filtered. These two filtrates were combined and passed through with a flow rate of 500 ml/hour on a column containing 138 g (250 ml) Dowex Al 400 (OH) resin (diameter of the column 3.4 cm, height of the resin bed: 28 cm), then the resin bed was washed with 300 ml deionized water. Subsequently, the elution from the resin was carried out by 1 liter acetone-water (1:1) mixture containing 10 g sodium chloride. The volume of the fractions was 100 ml each. The eluate was analyzed by the following thin layer chromatographic (TLC) method: adsorbent: Kieselgel 60 F$_{254}$ DC (Merck) aluminum foil; developing solvent: acetone-benzene-acetic acid (50:50:3) mixture; detection: with phosphomolybdic acid reagent. The $R_f$ value of pravastatin is 0.5. Fractions containing the product were combined and the acetone was distilled off in vacuum. The pH of the 400 ml concentrate was adjusted to 3.5–4.0 by 15% sulfuric acid, then it was extracted three times by 150 ml ethyl acetate. The ethyl acetate extracts were combined and dried with anhydrous sodium sulfate. Subsequently, pravastatin lactone was prepared from pravastatin acid by adding at room temperature under continuous stirring trifluoroacetic acid in catalytic amount. The formation of pravastatin lactone was controlled by TLC (the $R_f$ value of pravastatin lactone in the above TLC system is 0.7). After the completion of the lactone formation, the ethyl acetate was washed with 2×50 ml 5% aqueous sodium hydrogen carbonate solution, then washed with 50 ml water, dried with anhydrous sodium sulfate and evaporated in vacuum. The evaporation residue obtained in a quantity of 3 g was dissolved in 100 ml acetone and clarified with 0.3 g charcoal. Then the charcoal was filtered off and the acetone was evaporated in vacuum. The crude product obtained was crystallized from 20 ml ethanol. Precipitated crystalline pravastatin lactone was filtered off, and washed on the filter with 30 ml n-hexane and dried at room temperature in vacuum. In this way 1.5 g chromatographically pure pravastatin lactone was obtained. Melting point 140–142° C., $[\alpha]_D$=+194° (c=0.5, methanol). The mother liquor of the crystallization was evaporated in vacuum and 1.2 g evaporation residue is obtained, which was chromatographed on 24 g Kieselgel 60 adsorbent containing column (diameter of the column: 1.6 cm, height of the bed: 20 cm). The crude product dissolved in 5 ml benzene was layered on the column. For elution mixtures of ethyl acetate-n-hexane were used in which the ethyl acetate content was gradually increased. Pravastatin lactone can be eluted from the column with the mixture of 60% ethyl acetate –40% n-hexane. Fractions were controlled by TLC using the mixture of ethyl acetate-n-hexane (9:1) as the developing solvent. The pravastatin lactone-containing fractions were combined and evaporated in vacuum. According to this method 0.3 g pure product is obtained, its quality identical with that of the pravastatin lactone obtained by crystallization.

The two pravastatin lactone batches were combined and the sodium salt was prepared according to the following method: 1.8 g pravastatin lactone was dissolved in 20 ml acetone and under stirring 4.5 ml of IM aqueous sodium hydroxide was added, then the solution was stirred for half an hour at room temperature. When the salt formation was completed, 20 ml water was added into the mixture and the solution was neutralized, then the acetone was evaporated in vacuum. The aqueous concentrate was chromatographed on a column filled with 150 ml Diaion HP 20 resin (diameter of the column: 2.6 cm, height of the bed: 30 cm). As the eluting agent mixtures of acetone-deionized water were used, where the concentration of the acetone was increased in 5% steps. Pravastatin can be eluted from the column by a 15% acetone containing acetone-deionized water mixture. Fractions were analyzed by TLC. Fractions containing the product are combined and acetone was evaporated in vacuum. By lyophilization of the aqueous residue 1.3 g pravastatin was obtained. The chromatographically pure product was crystallized from a mixture of ethanol and ethyl acetate.

Melting point: 170–173° C. (decomp.)
$[\alpha]^P_{20}$=+156°, (c=0.5, in water).
Ultraviolet absorption spectrum (20 µg/ml, in methanol): $\lambda_{max}$=231, 237,245 nm
(log ε–4.263; 4.311; 4.136)
Infrared absorption spectrum (KBr): υOH 3415, υCH 2965, υC=O 1730, υCOO$^-$ 1575 cm$^{-1}$.
$^1$H-NMR spectrum (D$_2$O, δ, ppm): 0.86, d, 3H (2-CH$_3$); 5.92, dd, J=10.0 and 5.4 Hz, 1H (3-H); 5.99, d, J=10.0 Hz, 1H (4-H); 5.52, br 1H (5-H); 4.24, m 1H (6-H); 5.34, br, 1H (8-H); 4.06, m, 1H (β-H), 3.65, m, 1H (δ-H); 1.05, d, 3H (2'-CH$_3$); 0.82, t, 3H (4'-H$_3$).
$^{13}$C-NMR spectrum (D$_2$O, δ, ppm): 15.3, q (2-CH$_3$); 139.5, d (C-3); 129.5, d, (C-4); 138.1, s(C-4a), 127.7, d (C-5); 66.6, d (C-6); 70.1, d (C-8); 182.6 s (COO$^-$); 72.6. d (C-β); 73.0, d (C-δ); 182.0, s (C-1') 18.8; q (2'-CH$_3$); 13.7, q (C-4').
Positive FAB mass spectrum (characteristic ions):
[M+Na]$^+$ 469; [M+H]$^+$ 447.
Negative FAB mass spectrum (characteristic ions):
[M–H]$^-$ 445, [M–Na]$^-$ 423, m/z 101 [2-methyl-butyric acid-H]$^-$.

Example 3

In a laboratory scale fermenter with 5 liters working volume, bioconversion culture medium MU/4 was prepared as described in Example 1, although it was loaded up to 4.5 liters, the composition of the culture medium was calculated to 5 liters. Then it was sterilized for 45 min at 121° C. and inoculated with 500 ml of the inoculum culture made according to Example 1. The fermentation was carried out at 25° C. by the application of a stirring rate of 300 rpm and an aeration rate of 50 liters/hour for 4 days. After 5 g compactin substrate feeding to the culture the bioconversion was carried out according to the Example 2.

After finishing the bioconversion, the 4.9 liters broth, which contained 660 µg/ml pravastatin, was filtered and the separated mycelium was washed by suspension in 2×1 liter deionized water. The pH of the combined 5.6 liters filtrate of the broth was adjusted by 20% sulfuric acid to 3.5–3.7, then the acidic filtrate was stirred with 2750 ml ethyl acetate for 30 min. Subsequently, the phases are separated. The aqueous phase was extracted again with 2×1375 ml ethyl acetate. 470 ml deionized water was added to the combined 4740 ml ethyl acetate extract, then the pH of the aqueous ethyl acetate mixture was adjusted to 7.5–8.0 by 1M sodium hydroxide. After 20 min stirring the phases were separated, then the ethyl acetate extract was extracted with 2×235 ml deionized water as described above. Then the combined weakly alkaline aqueous solution of 1080 ml volume was concentrated in vacuum to 280 ml volume. The concentrated aqueous solution was layered on a chromatographic column (ratio of height:diameter=6.5) filled with 280 ml Diaion HP-20 (Mitsubishi Co., Japan) non-ionic resin. The adsorption on the column was carried out with a flow rate of 250–300 ml/hour, then the column was washed with 840 ml deionized water. Subsequently, the column was eluted in the following order with 800 ml 5%, 1000 ml 10%, 500 ml 15% and 500 ml 20% acetone-containing water. In the course of the elution 50 ml fractions were collected, which were analyzed by the TLC method given in the Example 2. Fractions containing pravastatin as the main component were combined and the obtained solution was concentrated in vacuum to 260 ml volume. The concentrated aqueous solution was chromatographed on a column containing Diaion HP-20 resin in 260 ml volume. After the adsorption of pravastatin the column was washed with 790 ml deionized water, then eluted with aqueous acetone solutions in 260–260 ml portions gradually increasing the acetone content as follows: 2.5, 5.0, 7.5, 10.0, 12.5, 15.0 and 20.0%. In the course of the column chromatography 25 ml fractions were collected, and the pravastatin content of the fractions was analyzed as given before. Fractions containing pravastatin as the single component by TLC were combined and evaporated in vacuum. Subsequently, 0.3 g charcoal was added to the concentrated aqueous solution (about 30 ml) and pravastatin was clarified at room temperature for 30 min. Then the charcoal was removed by filtration from the solution and the filtrate was lyophilized. In this way 1.62 g pravastatin was obtained in lyophilized form.

Example 4

From the slant culture of the *Mortierella maculata* nov. spec. E-97 [NCAIM(P)F 001266] strain cultivated for 10–12 days, a spore suspension was prepared with 5 ml sterile 0.9% sodium chloride solution, and this suspension was used to inoculate 500 ml VHIG inoculum medium being sterilized in 3000 ml Erlenmeyer flask.

Composition of the medium VHIG:

| glucose | 30 g |
| meat extract | 8 g |
| yeast extract | 1 g |
| Tween-80 (polyoxyethylene (20) sorbitan monooleate) | 0.5 g |
| in 1000 ml tap water. | |

Before the sterilization the pH of the medium was adjusted to 7.0 and the sterilization was carried out at 121° C. for 25 min. The culture was cultivated for 3 days on a rotary shaker (250 rpm, amplitude 2.5 cm), then the obtained inoculum culture was used to inoculate a laboratory scale fermenter containing bioconversion culture medium PK in 5 liters working volume.

Composition of the medium PK:

| glucose | 40 g |
| peptone | 5 g |
| soybean meal | 20 g |
| $K_2HPO_4$ | 2 g |
| $KH_2PO_4$ | 1 g |
| $NaNO_3$ | 2 g |
| KCl | 0.5 g |
| in 1000 ml tap water. | |

Before the sterilization the pH of the medium is adjusted to 7.0. After the inoculation, cultivation, the substrate feeding and bioconversion were carried out according to Example 2, then the pravastatin was isolated from the broth in which its concentration was 650 μg/ml at the end of the fermentation.

Finishing the fermentation, the pH of the 4.9 liters broth containing 650 μg/ml pravastatin was adjusted under continuous stirring with 2M sodium hydroxide to 9.5–10.0, then after one hour stirring the pH is adjusted to 3.5–3.7 with 20% sulfuric acid. Subsequently, the acidic solution was extracted with 2.45 liters ethyl acetate. The phases are separated, and with centrifugation a clear extract was prepared from the emulsified organic phase. The broth was extracted again with 2×1.22 liters ethyl acetate by the method given above. The ethyl acetate extracts were combined and 0.4 liters deionized water were added, then the pH of the mixture was adjusted to 8.0–8.5 with 1 M sodium hydroxide. Phases were separated, and the ethyl acetate phase was extracted with 2×0.2 liters deionized water of pH 8.0–8.5 as given above. The pH of the combined pravastatin containing weakly alkaline aqueous solution was adjusted under stirring with a 20% sulfuric acid solution to 3.5–3.7. The acidic solution obtained was extracted with 4×0.2 liters ethyl acetate. The combined ethyl acetate extracts are washed with 2×0.2 liters deionized water, then 150 mole % dibenzylamine —calculated for the pravastatin content measured by HPLC —was added into the ethyl acetate solution. The ethyl acetate solution was concentrated in vacuum to 0.2 liters volume. Further 20 mole % dibenzylamine was added to the concentrate obtained, and the precipitated solution was kept overnight at 0–5° C. The precipitated pravastatin dibenzylamine salt was filtered, then the precipitate was washed on the filter with cold ethyl acetate and then two times with n-hexane, and finally it is dried in vacuum at 40–50° C. The crude product obtained (3.9 g) was dissolved in 100 ml methanol at room temperature, then the solution was clarified by 0.45 g charcoal. Thereafter the methyl alcoholic filtrate is concentrated in vacuum. The evaporated residue was dissolved in 120 ml acetone at an external temperature of 62–66° C., then the solution was cooled to room temperature. Subsequently, the recrystallization was continued overnight at 0–5° C. Precipitated crystals were filtered, then the crystals were washed on the filter two times with cold acetone and two times with n-hexane. The recrystallized pravastatin dibenzylamine salt was suspended in the mixture of 160 ml isobutyl acetate and 80 ml deionized water. Subsequently, sodium hydroxide was added in an equivalent amount into the suspension under stirring. After the disappearance of the suspension the phases were separated and the pravastatin containing aqueous solution was washed with 2×30 ml isobutyl acetate. The aqueous solution obtained was clarified with charcoal. Then the aqueous filtrate was concentrated to about 20 ml volume. The aqueous solution obtained was loaded on a chromatographic column (height:diameter=22) filled with 0.4 liters Sephadex LH-20 gel (supplier: Pharmacia, Sweden). In the course of the chromatography deionized water was used as the eluent, and 20 ml fractions were collected. Fractions were analyzed by TLC, then those containing pravastatin also by HPLC using the methods described above. Fractions containing pure pravastatin were combined and lyophilized. In this way 1.75 g pravastatin was obtained, the purity of which is higher than 99.5% by HPLC.

Example 5

A spore suspension was prepared from the slant culture of the *Mortierella maculata* n. spec. E-97 [NCAIM(P)F 001266] strain cultivated for 10–12 days with 5 ml sterile 0.9% sodium chloride solution, and then 500 ml inoculum medium was inoculated with it as described in Example 4. In a laboratory scale fermenter with 5 liters working volume bioconversion culture medium PC/4 is sterilized for 45 min at 121° C. and then inoculated with the seed culture.

Composition of the medium PC/4:

| | |
|---|---|
| malt extract | 5.0% |
| soybean meal | 1.0% |
| peptone | 1.0% |
| corn steep liquor | 1.0% |
| MgSO$_4$ × 7 H$_2$O | 0.1% |
| in 1000 ml tap water. | |

Before the sterilization the pH of the medium is adjusted to 7.0. After the inoculation, the cultivation and substrate feeding were carried out according to the Example 2, and then 5.1 liters broth with a concentration of 610 µg/ml pravastatin was obtained.

From the broth 3.7 g pravastatin dibenzylamine salt crude product was produced by the method given in Example 4, from which after recrystallization 2.9 g pravastatin dibenzylamine salt was obtained. The recrystallized pravastatin dibenzylamine salt was suspended in 45 ml ethanol, then under stirring 110 mole % sodium hydroxide was added by the feeding of 1M ethanolic sodium hydroxide solution. Stirring of the solution is continued for half an hour, then 0.3 g charcoal was added into it and stirred for another half an hour. The solution was filtered, and the filtrate was concentrated to 15 ml. Then 60 ml acetone was added to the concentrate at 56–60° C. The solution obtained was cooled to room temperature, then kept overnight at +5° C. Subsequently, the precipitate was filtered, then washed with 2×20 ml acetone, 2×20 ml ethyl acetate and 2×20 ml n-hexane, and finally dried in vacuum. The resulting 1.7 g crude pravastatin was dissolved in ethanol, then clarified with charcoal and crystallized from an ethanol-ethyl acetate mixture. In this way 1.54 g pravastatin was obtained that was identical with the product of Example 2.

Example 6

As described in Example 4, from the slant culture of the *Mortierella maculata* n. spec. E-97 [NCAIM(P)F 001266] strain cultivated for 7–10 days, a 500 ml inoculum medium MI sterilized in a 3000 ml Erlenmeyer flask was inoculated and incubated at 28° C. for 3 days on a rotary shaker.

Composition of the medium MI:

| | |
|---|---|
| glucose | 40 g |
| casein | 5 g |
| KCl | 0.5 g |
| NaNO$_3$ | 3 g |
| KH$_2$PO$_4$ | 2 g |
| MgSO$_4$ × 7H$_2$O | 0.5 g |
| FeSO$_4$ × 7H$_2$O | 0.01 g |
| in 1000 ml tap water. | |

Before the sterilization the pH of the medium is adjusted to 6.0 and the sterilization is carried out at 121° C. for 35 min. The seed culture obtained is inoculated into 5 liters bioconversion medium P12 sterilized in a fermenter.

Composition of the medium P12:

| | |
|---|---|
| glucose | 10 g |
| malt extract | 50 g |
| yeast extract | 5 g |
| corn steep liquor | 5 g |
| MgSO$_4$ × 7H$_2$O | 1 g |
| Tween-80 | 0.5 g |
| in 1000 ml tap water. | |

Before the sterilization the pH of the medium is adjusted to 7.0, then the sterilization was carried out at 121° C. for 45 min. The fermentation, substrate feeding and bioconversion were carried out according to the Example 2. After finishing the bioconversion the pravastatin formed in the concentration of 620 µg/ml was isolated as follows:

The pH of 5.15 liters broth containing 620 µg/ml pravastatin was adjusted with 2M sodium hydroxide to 9.5 value then stirred at room temperature for 1 hour. The broth was filtered and the mycelium was washed with suspension in 1×2 liters and then 1×0.5 liters water. Filtrates are combined and the pH of the aqueous solution was adjusted with 20% sulfuric acid to 3.7 value and extracted with 2.5 liters then with 1.5 liters ethyl acetate. The ethyl acetate extracts were combined, washed with 2×0.5 liters water and 1.95 g dicyclohexylamine was added. The ethyl acetate extract was concentrated at 40° C. to 200 ml under reduced pressure, and 0.195 g dicyclohexylamine was added again into the concentrate, which was then stirred at 15° C. for 6 hours. The precipitated crystalline material was filtered, washed with 20 ml and with 15 ml ethyl acetate and dried at 40° C. In this way 3.51 g crude product was obtained. After the recrystallization of the crude product in an acetone-ethanol mixture, 3.05 g of pravastatin dicyclohexylamine salt was obtained (melting point: 162–168° C.), which was converted to pravastatin according to the Example 5.

Example 7

The fermentation, substrate feeding and bioconversion were carried out with the *Mortierella maculata* n. spec. E-97 [NCAIM(P)F 001266] strain as described in Example 2. Pravastatin obtained as a result of the bioconversion is isolated from the broth as follows.

5 liters culture broth containing in concentration 650 µg/ml pravastatin was filtered on a filter cloth. The mycelium of the mold was stirred in 2 liters 0.1M sodium hydroxide solution for an hour, then filtered. The two filtrates were combined and the pH was adjusted with 15% sulfuric acid to 3.5–4.0. Subsequently, the solution was extracted with 2×1.8 liters ethyl acetate. The combined ethyl acetate phases were washed with 800 ml water. Then 400 ml deionized water was added and the pH of the mixture is adjusted by 1M sodium hydroxide to a 8.0–8.5 value. The mixture was stirred for 15 minutes, then the phases were separated. 300 ml water was added to the ethyl acetate phase and the pH are adjusted to 8.0–8.5. After stirring for 15 minutes the phases were separated. 300 ml water was added again to the ethyl acetate phase and the pH was adjusted to 8.0–9.5. Then the mixture was stirred for 15 min. The two phases were separated again. All aqueous phases were combined and the pH are adjusted with 15% sulfuric acid to 3.5–4.0, then extracted with 3×300 ml ethyl acetate. The combined ethyl acetate extracts were washed with 150 ml water, dried with anhydrous sodium sulfate, and filtered. Then 150 mole % dioctylamine—calculated for the pravastatin content-was added to the ethyl acetate extract. The ethyl acetate was evaporated to about 1/10 volume and acetone was added until precipitation. The mixture was kept at +5° C. overnight. The precipitate was filtered on a G-4 filter, washed with 20 ml acetone and then with 20 ml n-hexane and dried in vacuum at room temperature. The 3.3 g crude pravastatin dioctylamine salt obtained was recrystallized from 20 ml acetone resulting in 2.7 g pure pravastatin dioctylamine salt. Melting point: 143–146° C. The pravastatin dioctylamine salt was converted to pravastatin with the method given in Example 5.

Example 8

By the development of the hydroxylation ability of *Mortierella maculata* n. spec. E-97 strain isolated from natural habitat, which is able to 6β-hydroxylate compactin, in the mutation-selection and enzyme induction experiments discussed in detail below, *Mortierella maculata* n. sp. E-97/15/13 [NCAIM(P)F 001267] mutant strain was produced.

*Mortierella maculata* n. sp. E-97 [NCAIM(P)F 001266] strain isolated by us was cultivated on MS slant agar medium at 28° C. for 7 days.

Composition of agar medium MS:

| | |
|---|---|
| glucose | 4 g |
| malt extract | 10 g |
| yeast extract | 4 g |
| agar | 20 g |
| in 1000 ml distilled water. | |

Spores were washed off from the slant cultures by 5 ml 0.9% sodium chloride solution, then after transferring the spore suspension into a sterile Petri dish it was irradiated by ultraviolet light for 1 minute. Subsequently, N-methyl-N'-nitro-N-nitrosoguanidine was added to the spore suspension in the final concentration of 2000 μg/ml. Then the suspension was transferred into a 100 ml Erlenmeyer flask and it was shaken at 28° C. with a rate of 150 rpm for 20 min. Subsequently, the spores were sedimented by centrifugation with a rate of 4000 rpm for 10 min, then suspended in sterile 0.9% sodium chloride solution. The suspension was spread on an agar plate MU-VB containing 10 μg/ml benomyl and 1% defibrillated blood.

Composition of agar medium MU-VB:

| | |
|---|---|
| glucose | 40 g |
| asparagine | 2 g |
| peptone | 2.5 g |
| potassium dihydrogen phosphate | 0.5 g |
| agar | 20 g | in 990 ml distilled water; after sterilization the medium was completed with 10 ml bovine blood and 10 mg benomyl.

The agar plates were incubated at 28° C. for 7 days, then the grown colonies were transferred by random selection into test tubes containing agar medium PS.

Composition of agar medium PS:

| | |
|---|---|
| glucose | 40 g |
| mycological peptone | 10 g |
| agar | 15 g |
| in 1000 ml distilled water. | |

Before sterilization the pH of the medium is adjusted to 5.6–5.7 value. The sterilization is carried out at 121° C. for 20 min.

Slant cultures were incubated at 28° C. for 12 days, and their pravastatin productivity was tested in shaken flask experiments as described in Example 1. *Mortierella maculata* n. sp. E-97/15/13 mutant strain was selected by this method, which yielded pravastatin exceeding 60% conversion rate from the applied compactin acid sodium salt substrate being in the concentration of 1000 μg/ml.

The hydroxylase enzyme of *Mortierella maculata* n. sp. E-97/15/13 strain was induced by the cultivation on MU-VB agar medium containing 100 μg/ml 8-de-(2-methyl-butyryl) compactin and/or compactin. After random selection of the grown colonies they were transferred into inducer containing MU-VB slants. Pravastatin productivity of the grown slant cultures was examined by the method written in the Example 1 with the difference that the compactin substrate feeding in the quantity of 500 μg/ml was carried out from the 4th day of the fermentation for further 11 days and the compactin sodium substrate was added gradually during the twelve days converted completely to pravastatin. By the end of the bioconversion carried out in 50 shake flask cultures from 30 g compactin sodium substrate the formation of 18.5 g pravastatin was measured by HPLC. Recovery of the pravastatin from the combined fermentation broths was carried out according to the following method.

After finishing the fermentation the pH of 5.5 liters broth with a pravastatin concentration of 3360 μg/ml was adjusted with 20% sulfuric acid solution to 3.5–3.7. Subsequently, the acidic solution was extracted by 2.75 liters ethyl acetate. Phases were separated, and a clear extract was prepared by centrifugation from the emulsified organic phase. Broth was extracted two more times with 1.37 liters ethyl acetate as previously described. The combined ethyl acetate extracts were washed with 2×1.15 liters deionized water, then 150 mole % dibenzylamine—calculated for the pravastatin content measured by HPLC—was added to the ethyl acetate solution. The ethyl acetate solution was concentrated in vacuum to about 0.23 liters volume. Further 20 mole % dibenzylamine was added to the concentrate and the precipitate solution was kept overnight at 0–5° C. Precipitated pravastatin acid dibenzylamine salt was filtered, then the precipitate was washed by suspending it in cooled ethyl acetate and then two times in n-hexane, finally dried at 40–50° C. in vacuum. The crude product obtained (22.4 g) was dissolved in 0.67 liters acetone at 62–66° C. temperature, and the solution was clarified with 2.2 g charcoal. After the clarification the acetone filtrate was concentrated in vacuum to 0.56 liters volume. Crystals precipitated from the concentrate were dissolved again at the above temperature, then the solution was cooled to room temperature. Subsequently, the recrystallization was continued overnight at 0–5° C. Precipitated crystals were filtered, and washed by suspension two times in cooled acetone and two times in n-hexane. Recrystallized pravastatin acid dibenzylamine salt was dried in vacuum at 40–50° C. Pravastatin acid dibenzylamine salt obtained (14.8 g) was dissolved at 40–44° C. in 740 ml ethyl acetate-ethanol (9:1) mixture, then 110 mole % sodium hydroxide was added to the solution in form of a 1M ethanolic solution. Stirring of the obtained precipitated solution was continued for half an hour at room temperature, then a complete precipitation was achieved as a result of the application or ice cooling for 1–1.5 hours. Subsequently, the precipitate was filtered and washed with 2×150 ml cooled ethyl acetate and 2×150 ml n-hexane, finally dried in vacuum at 40–50° C. The pravastatin obtained was dissolved in ethanol, clarified by 1.0 g charcoal, then crystallized from ethanol-ethyl acetate mixture. This way 9.4 g pravastatin was obtained, with physical constants corresponding to the data given in Example 2.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

We claim:

1. The sodium salt of pravastatin in a crystalline form.
2. The sodium salt of pravastatin according to claim 1, wherein the melting point is in the range of from about 170° C. to about 173° C.

* * * * *

UNITED STATES PATENT AND TRADEMARK OFFICE
CERTIFICATE OF CORRECTION

PATENT NO. : 6,750,366 B2
DATED : June 15, 2004
INVENTOR(S) : Antónia Jekkel et al.

It is certified that error appears in the above-identified patent and that said Letters Patent is hereby corrected as shown below:

Title page,
Item [75], Inventors, change "Antonia Jekkel" to -- Antónia Jekkel --; change "Attila Konya" to -- Attila Kónya --; change "Istvan Barta" to -- István Barta --; change "Eva Ilkoy" to -- Éva Ilkőy --; change "Gyorgy Somogyi" to -- György Somogyi --; change "Gabor Ambrus" to -- Gábor Ambrus --; change "Gyula Horvath" to -- Gyula Horváth --; change "Karoly Albrecht" to -- Károly Albrecht --; change "Istvan Szabo" to -- István Szabó --; change "Julianna Mozes nee Suto" to -- Julianna Mózes née Sütő --; change "Janso Salat" to -- János Salát --; change "Laszlo Birincsik" to -- László Birincsik --; change "Sandor Boros" to -- Sándor Boros --; change "Szod" to -- Sződ --; "Ildiko Láng" to -- Ildikó Lang --; and change "Margit Bidlo nee Igloy" to -- Margit Bidló née Iglóy --;
Item [56], References Cited, OTHER PUBLICATIONS,
"Chem Abs. 82:41565..." reference, " change "J. Neurol" to -- J. Neurol. --
"Endo, A. et al.," reference, change "J. Antibiot" to -- J. Antibiot. --
"Kuo, C.H. et al.," reference, change "rom" to -- from --
"A.T.M., Serajuddin et al.," reference, change "(HMG-CoA), Reductase" to -- (HMG-CoA) Reductase --; and change "Mevastatin, and" to -- Mevastatin and --

Column 1,
Line 49, change "detectable, At" to -- detectable. At --

Column 3,
Line 45, change "opposition" to -- 6β–position --

Column 4,
Line 19, change "8a,β-hydroxy-compactin" to -- 8aβ-hydroxy-compactin --

Column 6,
Line 1, change "activity show" to -- activity, show --
Lines 1-2, change "9.0 tolerate" to -- 9.0, tolerate --
TABLE 1, column *Mortierella thaxteri*, line 14, change "sporangra" to -- sporangia --

Column 8,
Line 44, change "0.5% Compactin" to -- 0.5%. Compactin --

Column 9,
Line 47, change "these" to -- the --
Line 61, change "a 24 carbon" to -- a 2-4 carbon --

UNITED STATES PATENT AND TRADEMARK OFFICE
CERTIFICATE OF CORRECTION

PATENT NO.     : 6,750,366 B2
DATED          : June 15, 2004
INVENTOR(S)    : Antónia Jekkel et al.

It is certified that error appears in the above-identified patent and that said Letters Patent is hereby corrected as shown below:

Column 10,
Line 26, change "artefacts" to -- artifacts --
Line 28, change "Dextran" to -- dextran --
Line 35, change "nitrate" to -- filtrate --

Column 12,
Line 27, change "MU/S" to -- MU/8 --
Line 29, change "liters, volume" to -- liters volume --

Column 13,
Line 7, change "column" to -- column: --
Line 61, change "IM" to --1M --

Column 14,
Line 16, change "log ε - 4.263;" to -- log ε = 4.263; --
Line 21, change "br 1H" to -- br, 1H --
Line 21, change "m 1H" to -- m, 1H --

Column 18,
Line 59, change "and the pH are" to -- and after the pH was --

Column 19,
Between lines 49 and 50, inside the table, insert -- in 990 ml distilled water. --
Line 51, delete "in 990 ml distilled water;"
Line 51, change "after" to -- After --

Column 20,
Line 17, change "substrate was added" to -- substrate added --
Lines 37-38, change "precipitate" to -- precipitated --

UNITED STATES PATENT AND TRADEMARK OFFICE
CERTIFICATE OF CORRECTION

PATENT NO. : 6,750,366 B2
DATED : June 15, 2004
INVENTOR(S) : Antónia Jekkel et al.

It is certified that error appears in the above-identified patent and that said Letters Patent is hereby corrected as shown below:

Column 20 (cont'd),
Line 60, change "or" to -- of --

Signed and Sealed this

Twelfth Day of July, 2005

JON W. DUDAS
*Director of the United States Patent and Trademark Office*